US008622738B2

(12) United States Patent
Johnston

(10) Patent No.: US 8,622,738 B2
(45) Date of Patent: *Jan. 7, 2014

(54) ORTHODONTIC BRACE SYSTEM AND METHOD

(71) Applicant: Michael Stuart Johnston, Simpsonville, SC (US)

(72) Inventor: Michael Stuart Johnston, Simpsonville, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/708,148

(22) Filed: Dec. 7, 2012

(65) Prior Publication Data

US 2013/0095447 A1 Apr. 18, 2013

Related U.S. Application Data

(63) Continuation-in-part of application No. 12/967,445, filed on Dec. 14, 2010, now Pat. No. 8,383,699.

(51) Int. Cl.
*A61C 3/00* (2006.01)

(52) U.S. Cl.
USPC ............................................................ 433/10

(58) Field of Classification Search
USPC ................ 433/8, 9, 10, 11, 12, 13, 14, 15, 16
See application file for complete search history.

(56) References Cited

U.S. PATENT DOCUMENTS

| | | | | |
|---|---|---|---|---|
| 2,686,365 A * | 8/1954 | Schurter | | 433/14 |
| 3,218,713 A * | 11/1965 | Wallshein | | 433/11 |
| 3,421,221 A * | 1/1969 | Silverman et al. | | 433/8 |
| 3,775,850 A * | 12/1973 | Northcutt | | 433/16 |
| 4,415,330 A * | 11/1983 | Daisley et al. | | 433/16 |
| 4,597,739 A * | 7/1986 | Rosenberg | | 433/16 |
| 4,867,678 A * | 9/1989 | Parker | | 433/8 |
| 5,160,261 A * | 11/1992 | Peterson | | 433/8 |
| 5,275,557 A * | 1/1994 | Damon | | 433/10 |
| 6,247,923 B1 * | 6/2001 | Vashi | | 433/10 |
| 6,354,833 B1 * | 3/2002 | Townsend-Hansen | | 433/8 |
| 6,682,345 B2 * | 1/2004 | Kesling et al. | | 433/8 |
| 7,306,457 B2 * | 12/2007 | Vigolo | | 433/10 |
| 8,353,699 B2 * | 1/2013 | Johnston | | 433/8 |
| 2001/0038991 A1 * | 11/2001 | Nicola et al. | | 433/8 |
| 2007/0009849 A1 * | 1/2007 | Wool | | 433/10 |
| 2009/0136889 A1 * | 5/2009 | Abels et al. | | 433/10 |

* cited by examiner

*Primary Examiner* — Ralph Lewis
(74) *Attorney, Agent, or Firm* — Southeast IP Group, LLC; Thomas L. Moses

(57) ABSTRACT

An orthodontic brace system includes brackets having a diamond-shaped tie-wing configuration that defines two parallel, horizontal slots, each of which is adapted to receive an archwire. Each slot is angled with respect to the base of the bracket to produce a specific, maximum torque value, and generally, the maximum torque value of the gingival slot is less than the maximum torque value of the incisal slot. The brackets provide multiple force vectors in different directions simultaneously, which decreases the amount of time required for a patient to wear braces, reduces the number of costly and time consuming visits to an orthodontist, and reduces time and effort required of an orthodontist for installation and adjustment of the braces on a per visit basis. A self-ligating bracket with a sliding door is disclosed in another embodiment.

15 Claims, 12 Drawing Sheets

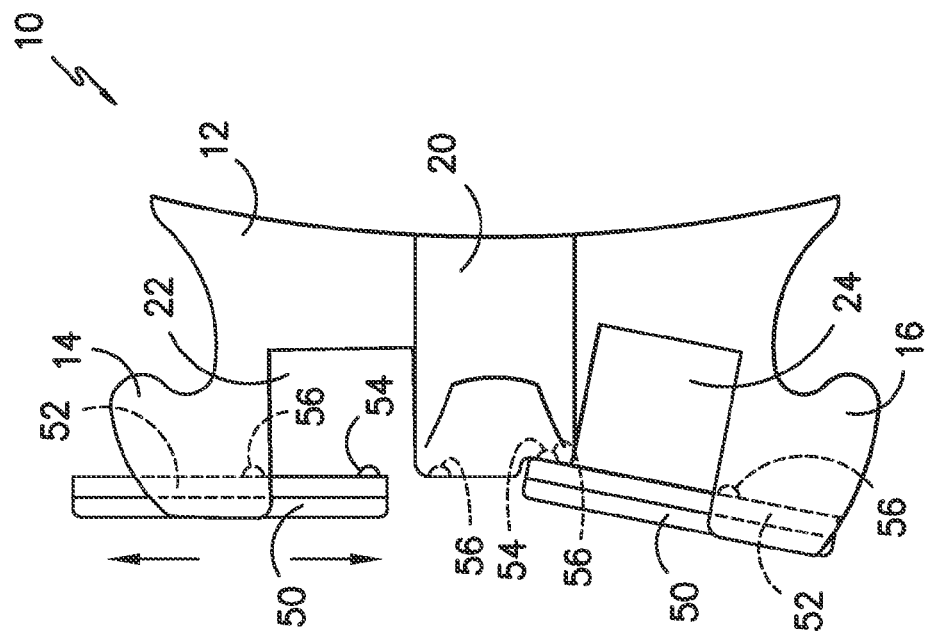
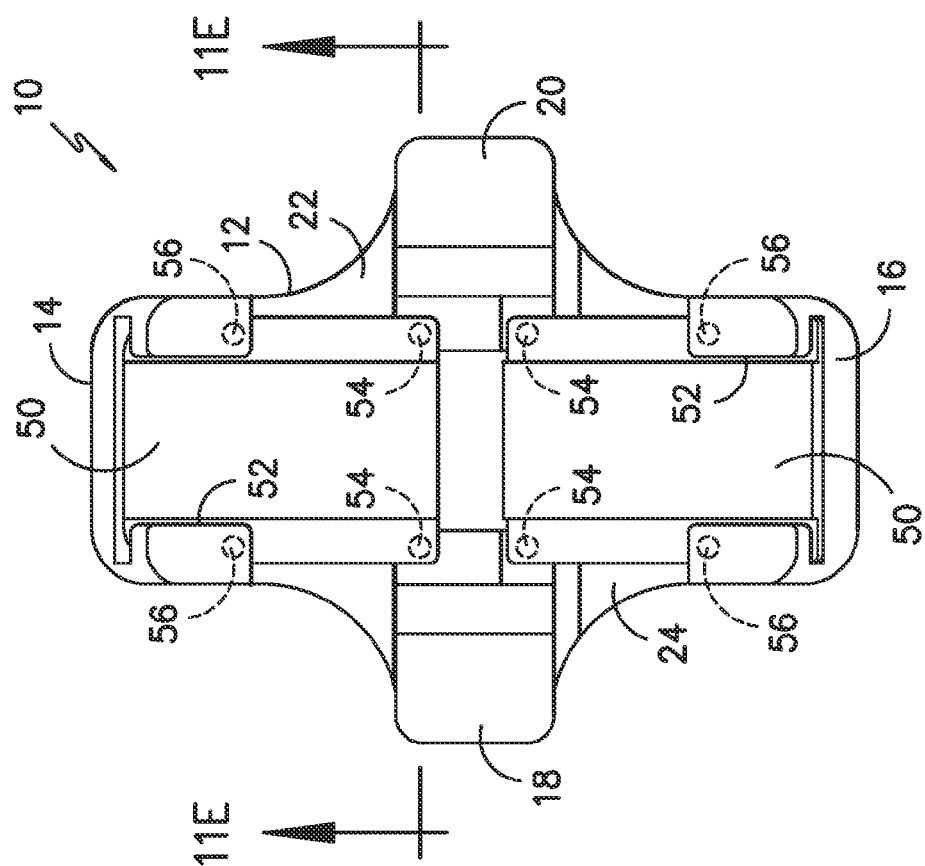

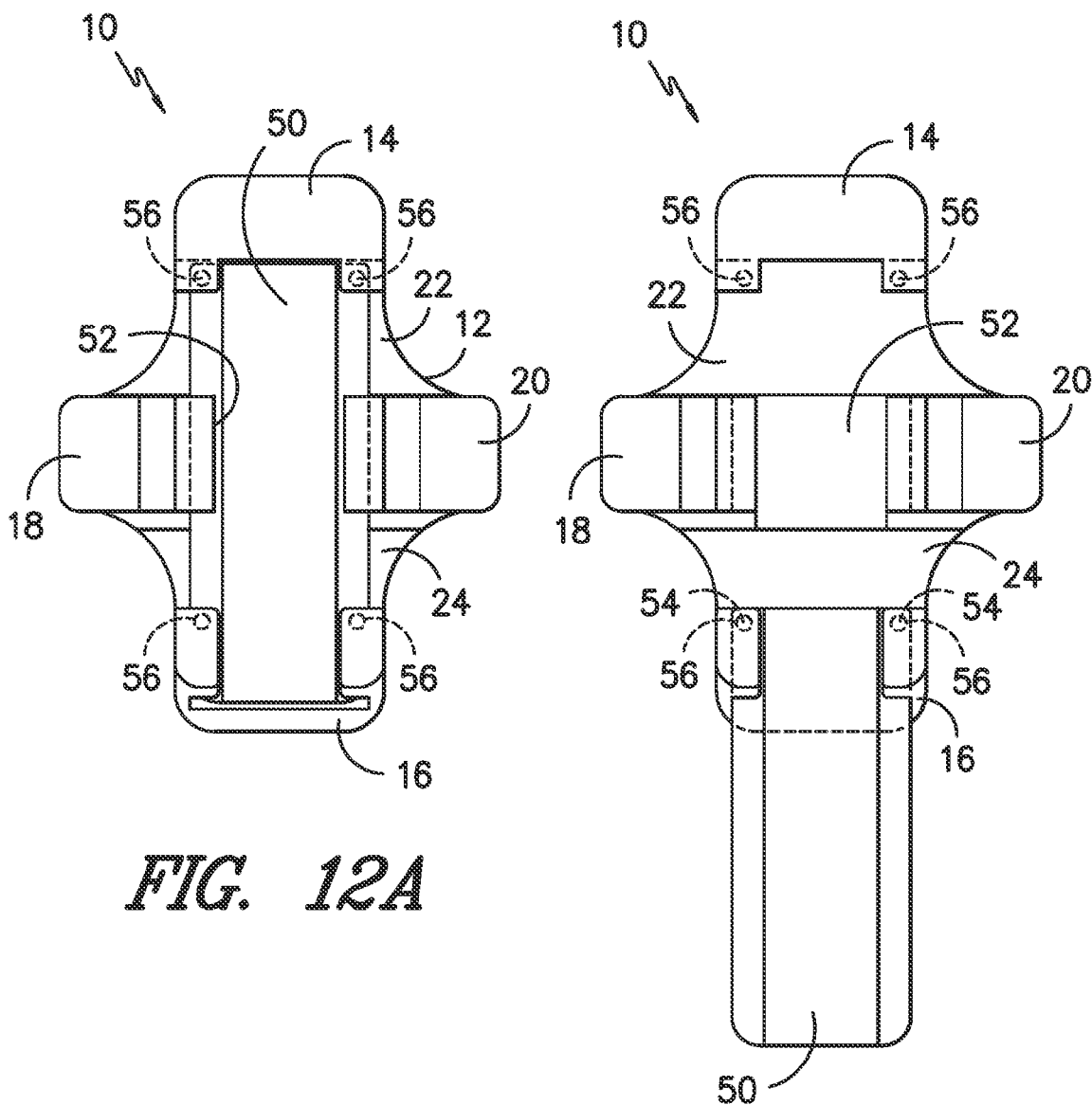

ORTHODONTIC BRACE SYSTEM AND METHOD

RELATED APPLICATIONS

This application is a continuation-in-part of U.S. application Ser. No. 12/967,445, filed on Dec. 14, 2010.

BACKGROUND OF THE INVENTION

The present invention relates generally to orthodontic braces and orthodontic brace systems used to straighten a patient's teeth. More specifically, the present invention includes a brace system wherein the brackets that are affixed to a patient's teeth are configured with multiple slots for receiving an archwire, so that an orthodontist may have increased flexibility in routing the archwire throughout brackets aligned along a row of teeth.

Heretofore, many different types of orthodontic braces have been developed and commercialized. Orthodontic treatment of teeth is accomplished by applying force to the teeth with archwires positioned in the channels or slots positioned on attachments on the teeth which are called brackets. Generally, these brackets are applied to the front of a patient's teeth, and include a single slot for receiving an archwire, which is oftentimes held in place within the slots by using small elastic bands (sometimes referred to as "elastic ligatures," or "elastic modules") that fit over the front of the archwire and are secured around tie-wings positioned on the bracket. Archwires are bent, shaped, and tightened frequently to achieve the desired results. Inter-arch elastics (often referred to as "rubber bands") are attached from one bracket to another or from one archwire to another in order to move teeth and improve the bite relationship. The placement and configuration of the inter-arch elastics will depend on the course of treatment and the individual patient. Inter-arch elastics are made in different diameters, colors, sizes, and strengths. Modern orthodontics makes frequent use of nickel-titanium archwires and temperature-sensitive materials. When cold, the heat-activated archwire is limp and flexible, easily threaded between brackets of any configuration. Once heated to body temperature, the archwire will stiffen and seek to retain its original shape, creating constant light force on the teeth. Other types of archwires are not heat activated, and have what is referred to as "memory," meaning that they may be bent in any direction but seek to retain their original straight configuration, without regard to any temperature differential.

Every few months, the braces must be adjusted. This adjustment helps shift the teeth into the correct position. When the braces are adjusted, the elastic ligatures keeping the wire in place are removed. The wire is then taken out, and may be replaced or modified. Sometimes, as the teeth have shifted due to the pressure from the archwire, adjustments require that the archwire be removed, and then often require that one or more brackets be removed and repositioned on that particular tooth. Brackets are repositioned in order to obtain the optimal site on the teeth to provide the necessary leverage and torque to continue moving the teeth along the path to proper alignment. Removing and repositioning a bracket is a costly, time consuming process. Additionally, brackets are manufactured to include a specific amount of maximum torque by providing a slot that is disposed at a particular angle with respect to the teeth. Thus, orthodontists must keep a large inventory of a variety of different brackets, in order to have brackets with proper torque levels on hand for orthodontic procedures.

Thus, it would be desirable to provide an orthodontic bracket and system that is configured to reduce time spent adjusting the archwire, and which is designed to reduce instances where a bracket must be removed and repositioned on a particular tooth. There exists a need for a novel, flexible bracket system, wherein the bracket includes multiple slots that are capable of receiving the archwire. Additionally, it would be desirable to provide a bracket that includes a diamond-shaped tie-wing configuration that allows the archwire to be threaded through in multiple directions and orientations, depending on the direction, torque and pressure required to align a specific tooth. Further, it would be desirable to provide a bracket with multiple archwire slots, wherein each horizontal slot is configured to include a different level of maximum torque (otherwise known as inclination), thereby reducing the amount of brackets that an orthodontist must maintain in inventory. Additionally, it would be desirable to provide a bracket with multiple archwire slots, further including a self-ligating element in the form of a hinged or sliding door that may be easily opened and closed by an orthodontist for inserting, adjusting and securing the archwire therein.

BRIEF SUMMARY OF THE INVENTION

In accordance with one aspect of the invention, an orthodontic bracket includes four tie-wings, wherein a single upper tie wing is provided together with a single lower tie wing, and a pair of opposed side tie wings are disposed therebetween, one on the left hand side, and one on the right hand side. This configuration defines two parallel horizontal slots, one upper slot being positioned between the upper tie wing and the two side tie-wings, and a lower slot, positioned between the lower tie-wing and the two side tie-wings. Each horizontal slot is configured to provide a different, specific amount of maximum torque when the archwire is applied. Additionally, a vertical slot is positioned between the two side tie-wings, beneath the upper tie wing and above the lower tie-wing.

In one embodiment of the present invention, an archwire may be threaded through and secured within the upper slot or the lower slot, depending upon the position of the particular tooth, and further depending on the orientation and pressure requirements of that tooth. Alternatively, the archwire may be threaded through the bracket so that it enters the bracket through the upper slot, and is then threaded downwardly through the vertical slot and through the lower slot on an opposed side of the bracket, creating a wave-shape in the archwire for that particular bracket. Conversely, the archwire may be threaded in the opposite manner through a bracket, so that the archwire enters the lower slot on one side, is threaded upwardly through the vertical slot, and is then threaded through the upper slot on the opposed side. The archwire may be directed through the bracket in any of these configurations, depending on the current orientation and position of the tooth, and further depending on where torque or pressure must be applied in order to align the tooth within the row of teeth.

In another embodiment, the bracket may include a self-ligating element in the form of a hinged or sliding door, which may obviate or reduce the need to use elastics to secure the archwire to the bracket. The self ligating bracket may include a door or doors that may provide access to the bracket slots, when in an open position, and which may be used to secure the archwire to the bracket, when the door is in the closed position. A single door may be used to cover a single slot or multiple slots. Alternatively, multiple doors may be used, each covering a single slot. In yet another embodiment, a bracket having a pair of slots may include a single door to cover a single slot, and elastics may be used to secure the archwire to the slot having no door.

BRIEF DESCRIPTION OF THE DRAWINGS

These and other features, aspects, and advantages of the present invention will become better understood with regard to the following description, appended claims, and accompanying drawings where:

FIG. 11B shows a front view of an orthodontic bracket in accordance with the embodiment shown in FIG. 11A, wherein the sliding doors are shown in a closed position;

FIG. 11C shows a side view of an orthodontic bracket in accordance with the embodiment shown in FIGS. 11A and 11B, wherein the lower door is shown in a closed position over the lower slot, and the upper door is shown in a partially open position over the upper slot;

FIG. 12A shows a front view of an orthodontic bracket in accordance with another embodiment of the present invention, wherein a single sliding door is disposed in a closed positioned over both the upper and lower slots of the bracket;

FIG. 12B shows a front view of an orthodontic bracket in accordance with the embodiment shown in FIG. 12A, wherein the sliding door is positioned in an open position, allowing access to both the upper and lower slots of the bracket;

DETAILED DESCRIPTION OF THE INVENTION

Figure 1:
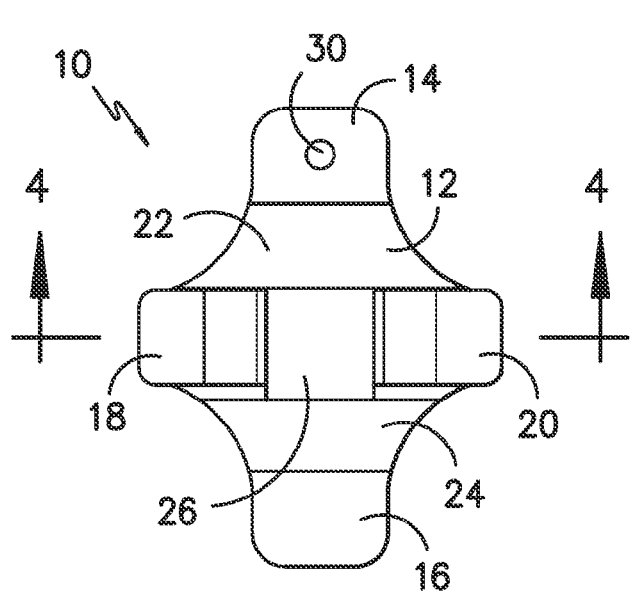
FIG. 1 is a front view of an orthodontic bracket, in accordance with one aspect of the present invention.

A first embodiment of an orthodontic brace bracket 10 is shown in FIG. 1. The bracket 10 includes a base member 12 having four tie-wings in a diamond-shaped configuration. A single upper tie-wing 14 is provided on an upper portion of the bracket, and a single lower tie-wing 16 is provided on a lower portion of the bracket 10. A left tie-wing 18 is provided on the left side of the bracket 10 and a right tie-wing 20 is provided on the right side thereof. The tie-wings define a pair of horizontal, parallel slots, including an upper slot 22 and a lower slot 24. Each horizontal slot 22, 24 is formed to define a specific angle in order to provide a specific, maximum amount of torque. Each bracket 10 is also configured to provide a specified angulation for each tooth. Additionally, a vertical slot 26 is positioned between the two side tie-wings 18, 20, beneath the upper tie-wing 14 and above the lower tie-wing 16.

Figure 5:
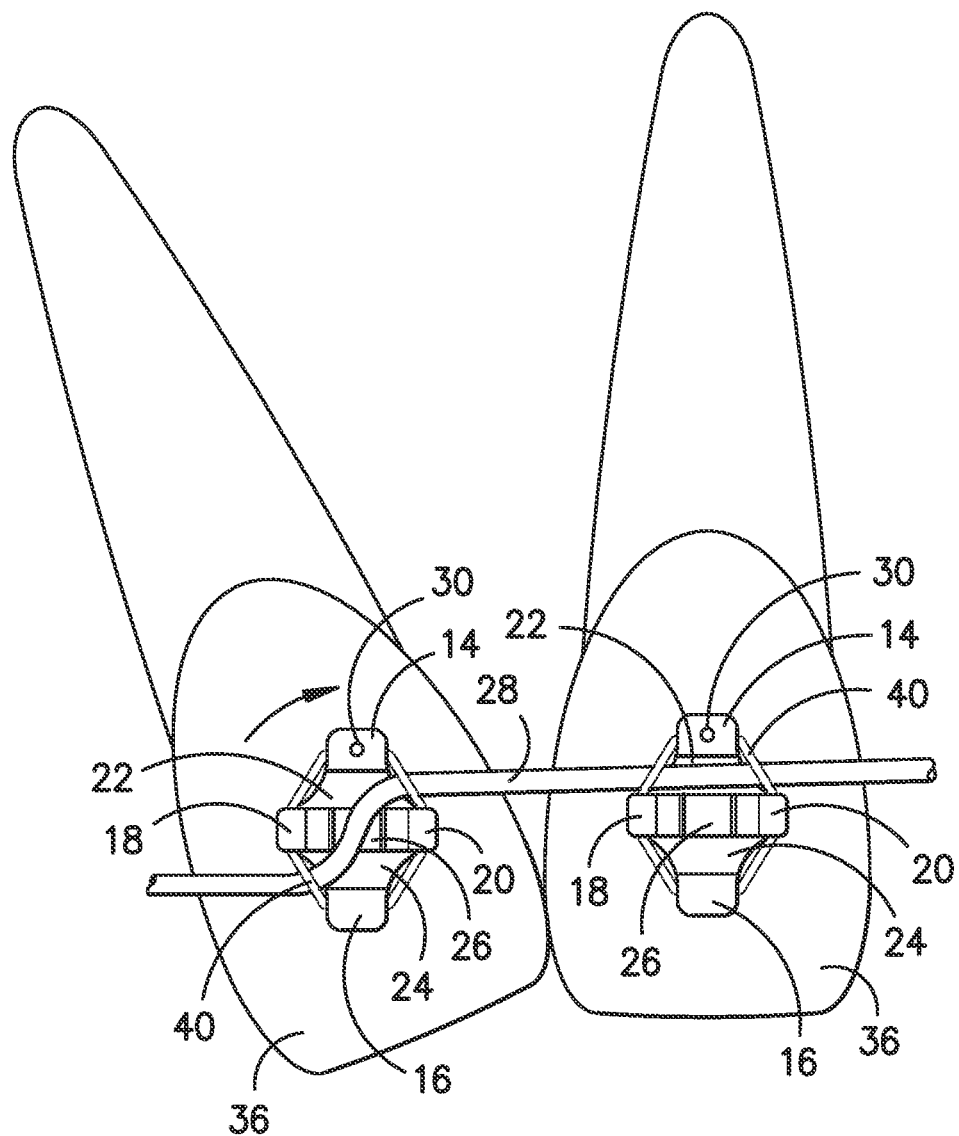
FIG. 5 is a front view of a pair of teeth, each having an orthodontic bracket positioned thereon, and an archwire threaded through an upper slot of one bracket on one tooth, and which further extends through a portion of the upper slot, down the vertical slot, and out the bottom slot within the bracket on the other tooth.

This diamond-shaped configuration of the tie-wings allows an archwire 28 to be threaded through the bracket 10 in several paths. The archwire 28 may be threaded through either the upper slot 22 or the lower slot 24, depending upon how the particular tooth is situated, and further depending on the pressure and torque that must be applied to the tooth in order to achieve proper alignment. Alternatively, the archwire 28 may be threaded through the lower slot 24, then up through the vertical slot 26, and then through the upper slot 22 on the opposed side, creating a wave configuration as shown in FIG. 5. Conversely, the archwire 28 may be threaded through the upper slot 22, then downwardly through the vertical slot 26, and finally out through the lower slot 24 on the opposed side. In some cases, two archwires 28 may be utilized simultaneously, with one archwire 28 in the upper slot 22 and another in the lower slot 24.

Figure 2:
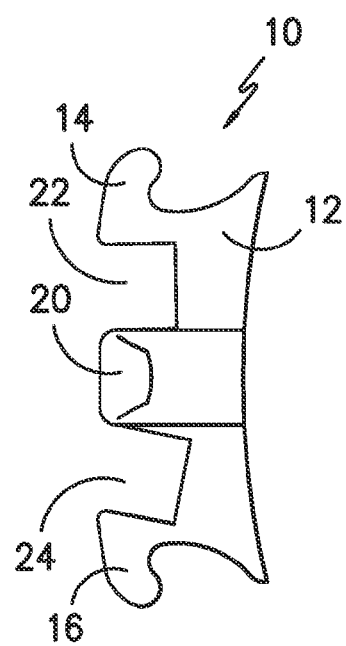
FIG. 2 is a side view of an orthodontic bracket, in accordance with one aspect of the present invention.
Figure 3:
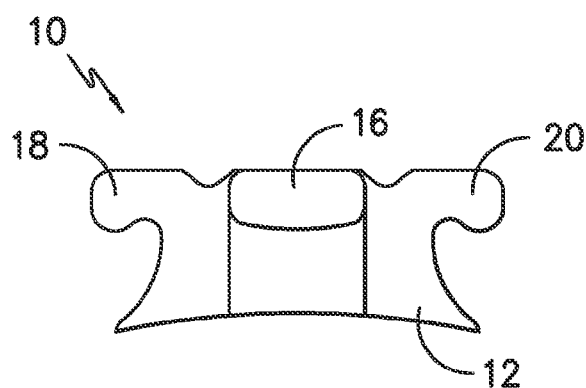
FIG. 3 is a bottom view of an orthodontic bracket, in accordance with one aspect of the present invention.
Figure 4:
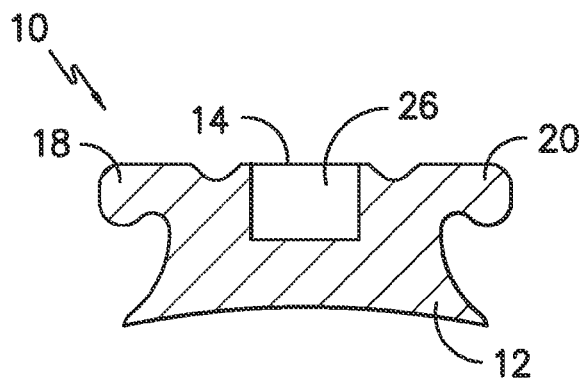
FIG. 4 is a cross-sectional view of an orthodontic bracket along the line 4-4 shown in FIG. 1, in accordance with one aspect of the present invention.

The parallel, horizontal slots 22, 24 are configured so that each slot is disposed at a different angle, as shown in FIGS. 1 and 2. The angular configuration of each slot determines the maximum amount of torque that may be applied to the bracket 10, and thus, the corresponding tooth. In a preferred embodiment, the gingival slot (closest to the patient's gumline) generally defines a lesser angle, and thus is configured to allow a lower value of maximum torque. The incisal slot (farthest from the gumline) in a preferred embodiment generally defines a greater angle, and thus is configured to allow a greater value of maximum torque. Typically, the gingival slot is configured to allow maximum torque in the range of about −33° to about 22°, and in a more preferred embodiment, the range is −22° to about 12°. The incisal slot is configured to allow maximum torque in the range of about −22° to about 33°, and in a more preferred embodiment, the range is about −15° to about 22°. The most preferred torque values for individual teeth are set forth in Table 1:

| Bracket | Degrees: Gingival Slot Torque | Degrees: Incisal Slot Torque |
| --- | --- | --- |
| Maxillary Central Incisor | 12 | 22 |
| Maxillary Lateral Incisor | 5 | 15 |
| Maxillary Canine | 0 | 6 |
| Maxillary Premolars | −9 | −4 |

-continued

| Bracket | Degrees: Gingival Slot Torque | Degrees: Incisal Slot Torque |
| --- | --- | --- |
| Mandibular Central and Lateral Incisors | −7 | 3 |
| Mandibular Canine | −8 | 7 |
| Mandibular First Premolar | −14 | −12 |
| Mandibular Second Premolar | −17 | −15 |

Figure 10A:
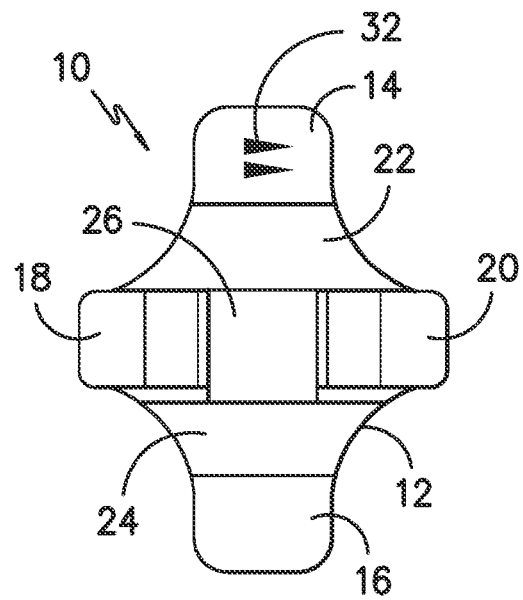
FIG. 10A shows a front view of an orthodontic bracket in accordance with one aspect of the present invention, including a triangular marker on an upper portion thereof, wherein the triangular marker includes two triangular shapes pointing toward the right, which designates a maxillary left bracket.
Figure 10B:
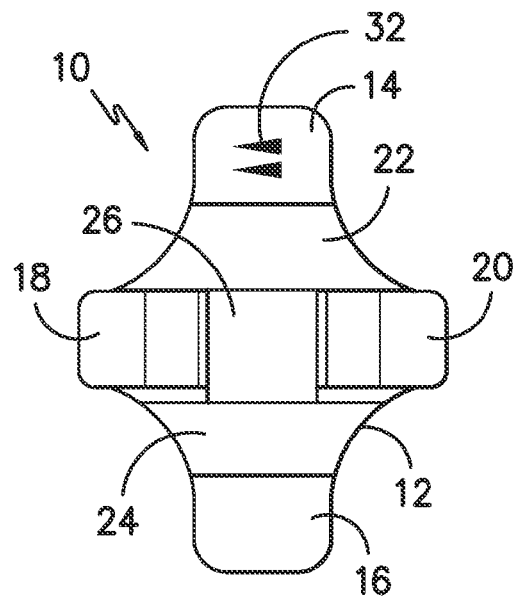
FIG. 10B shows a front view of an orthodontic bracket in accordance with one aspect of the present invention, including a triangular marker on an upper portion thereof, wherein the triangular marker includes two triangular shapes pointing toward the left, which designates a maxillary right bracket.
Figure 10C:
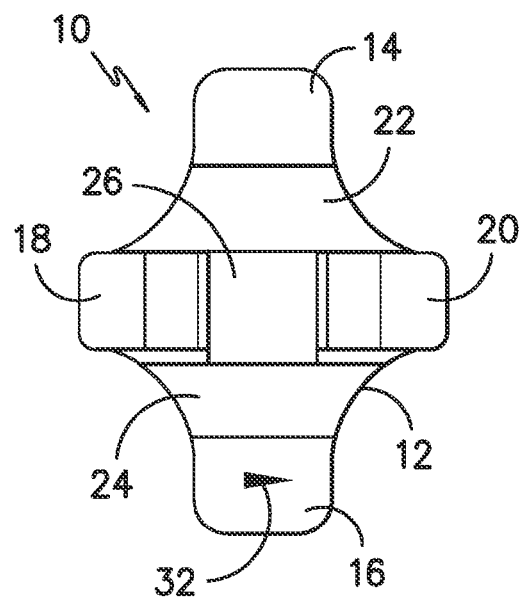
FIG. 10C shows a front view of an orthodontic bracket in accordance with one aspect of the present invention, including a triangular marker on a lower portion thereof, wherein the triangular marker includes a triangular shape pointing toward the right, which designates a mandibular left bracket.
Figure 10D:
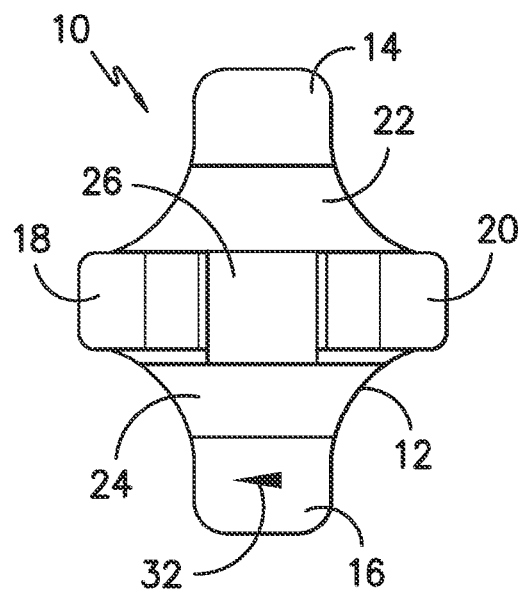
FIG. 10D shows a front view of an orthodontic bracket in accordance with one aspect of the present invention, including a triangular marker on a lower portion thereof, wherein the triangular marker includes a triangular shape pointing toward the left, which designates a mandibular right bracket.

For purposes of clarity, for maxillary brackets (adhered to upper teeth), the gingival slot is the upper slot 22 and the incisal slot is the lower slot 24. Conversely, for mandibular brackets (adhered to lower teeth), the gingival slot is the lower slot 24 and the incisal slot is the upper slot 22. Optionally, a small indention 30 (FIG. 1) or triangular marker 32 (FIGS. 10A-10D) may be placed on the gingival tie-wing to show how the bracket 10 should be oriented on a patient's tooth. The triangular marker 32 points left to indicate that the bracket 10 is designed for the right side of the dental arch. Conversely, the triangular marker 32 points right to indicate that the bracket is designed for the left side of the dental arch. Maxillary brackets are designated by two triangular markers 32 (FIGS. 10A and 10B) while the mandibular brackets are designated by one triangular marker 32 (FIGS. 10C and 10D).

The brackets 10 may be specifically configured for particular teeth. For instance, the brackets 10 used for mandibular central incisors and mandibular lateral incisors may be interchangeable, with maximum torque for the gingival slot configured to be −11° and maximum torque for the incisal slot configured to be −1°, for instance, with 0° angulation. The brackets 10 for the first maxillary premolar and the second maxillary premolar on the right side may be interchangeable with one another, and the brackets 10 for first maxillary premolar and second maxillary premolar on the left side may also be interchangeable.

With respect to corresponding contralateral brackets, some brackets 10 are designed to be mirror images of each other, largely due to the angulation factor (or, more simply stated, angulation). The angulation factor, for purposes of clarity, means that certain teeth 36, when properly aligned, are slightly angled toward a central point (such as the midline between the central incisors). For instance, the maxillary left lateral incisor bracket 10 may be configured to include a maximum torque of 8° in the gingival slot and a maximum torque of 14° in the incisal slot, with 9° angulation, while the maxillary right lateral incisor bracket is simply the mirror image of the left, thus including a −9° angulation factor. The maxillary left central incisor bracket 10 may be configured so that the gingival slot is configured to include maximum torque of 12° and the incisal slot is configured to include a maximum torque of 22°, with an angulation factor of 5°, while the maxillary right central incisor bracket is a mirror image thereof, with an angulation factor of −5°. It should be understood that the maximum torque of each slot and the angulation factor may be varied during the manufacturing process, as desired, and the above numerical values assigned for torque and angulation are merely examples of a preferred embodiment. Additionally, as described herein, torque values are the maximum torque values for a specific slot, and it is common to place a lower gauge archwire 28 through a slot so that the amount of torque applied to the tooth 36 is less than the maximum torque available for that slot.

Overall, the brackets may be manufactured to account for several variables, including the size of the bracket 10 (which should be proportional to the size of the tooth), the angulation of the bracket and the maximum torque of each slot. Typically, each rectangular slot has an opening or either approximately 0.022 inches or approximately 0.018 inches, although it is contemplated that larger or smaller slots may be used within the scope of the invention. A single bracket 10 may include two 0.022 inch slots, two 0.018 inch slots, or one 0.022 inch slot and one 0.018 inch slot.

The diamond shaped tie-wing configuration of the brackets 10 allows the present orthodontic brace system to be more flexible than other types of systems. Orthodontists may elect to use the gingival slots for non-extraction cases (requiring less torque), and for Dolichofacial patients, and may use the incisal slot for extraction cases (requiring more torque) and for Brachyfacial patients. The present system is also particularly useful for deep bite correction and open bite correction. Advantageously, the present system may be used to address all of these situations.

Figure 6A:
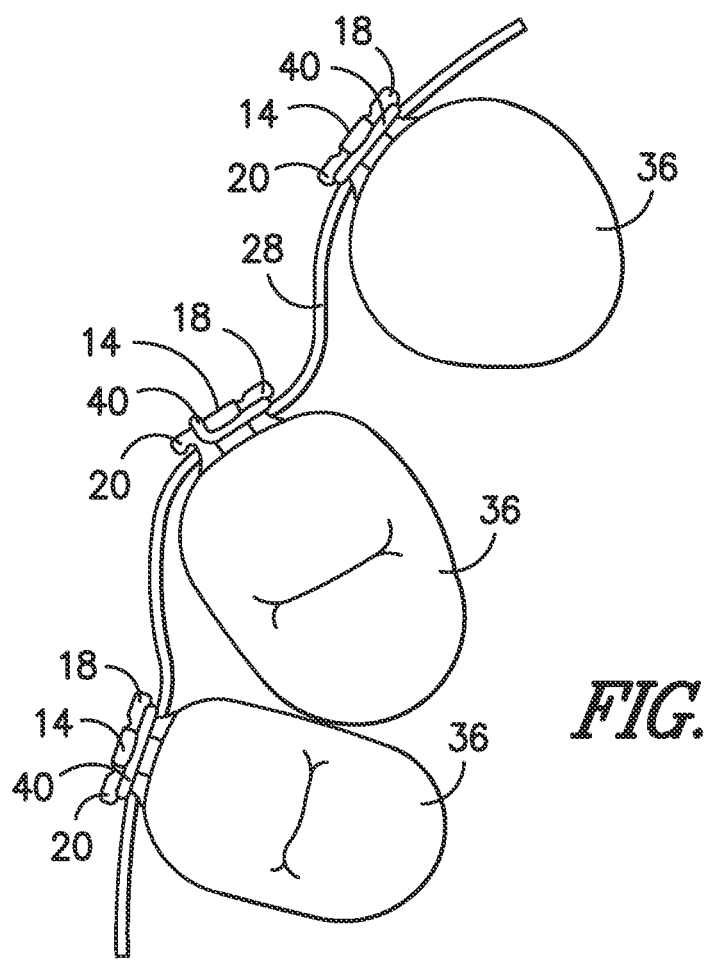
FIG. 6A is a bottom view (or occlusal view) of three maxillary teeth, wherein the middle tooth is rotated mesial-in, and further illustrating orthodontic brackets attached to each tooth with an archwire connected to the brackets, in accordance with one aspect of the present invention.
Figure 6B:
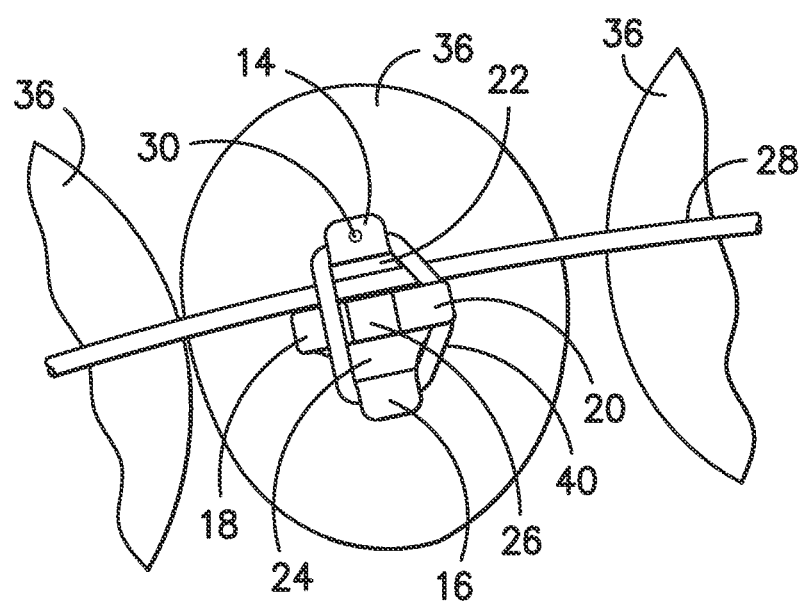
FIG. 6B is a front view of the teeth shown in FIG. 6A, further illustrating that the bracket attached to the middle tooth, which is rotated mesial-in, includes an elastic disposed about three of the four tie-wings, in accordance with one aspect of the present invention.

Additionally, the present system provides increased flexibility in the use and configuration of elastic ligatures. Typical orthodontic brackets require that the elastic ligatures be secured around all four tie-wings, in order to secure the archwire to the bracket. However, the present system allows an orthodontist to choose between using two tie-wings, three tie-wings or four tie-wings, depending upon how the tooth is situated and what force vectors are required for proper alignment. For instance, if a particular tooth 36 is rotated in a mesial-in direction, an orthodontist may attach the elastic ligature 40 to the upper tie-wing 14, the lower tie-wing 16 and the mesial tie-wing to de-rotate the tooth 36, as shown in FIGS. 6A and 6B.

Figure 9A:
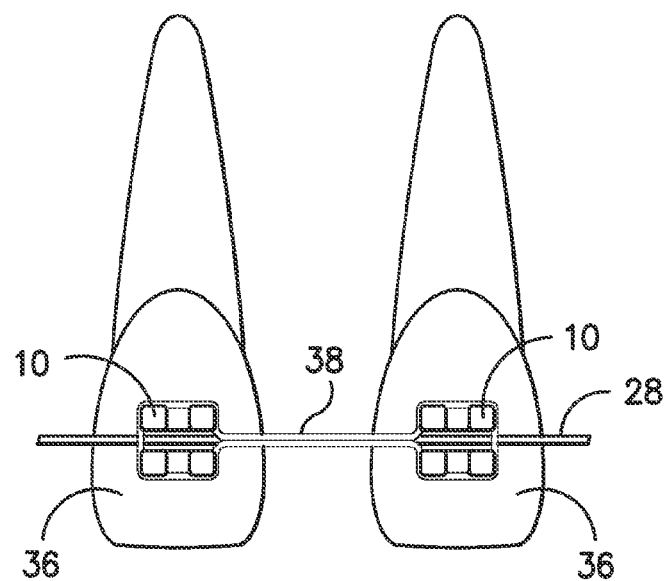
FIG. 9A includes a front view of two teeth having a gap therebetween, wherein each tooth includes a prior art bracket, with a small gauge archwire and an elastic power chain attached to the brackets.
Figure 9B:
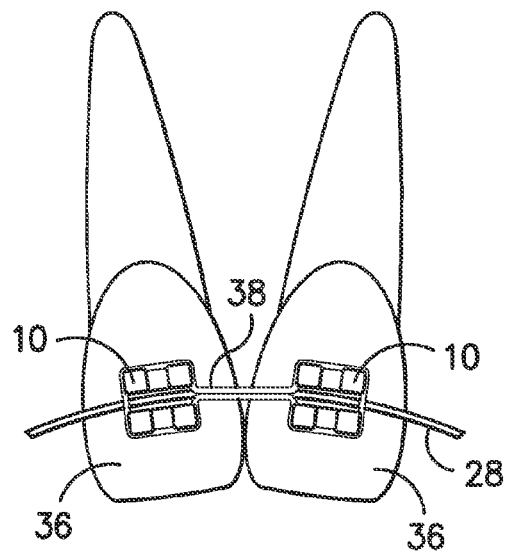
FIG. 9B shows a front view of the two teeth shown in FIG. 9A, showing the natural result and progression of the prior art orthodontics, wherein the crowns of the teeth have been brought together, and the roots are spaced apart.
Figure 9C:
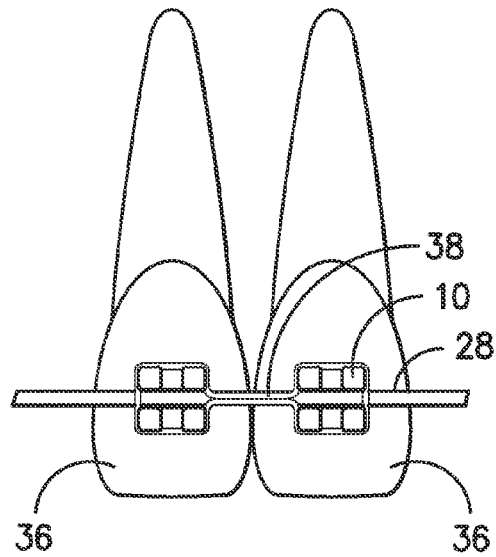
FIG. 9C shows a front view of the two teeth shown in FIG. 9B, wherein a heavier gauge archwire has replaced the small gauge archwire within the brackets, resulting in the roots of the teeth coming together.
Figure 9D:
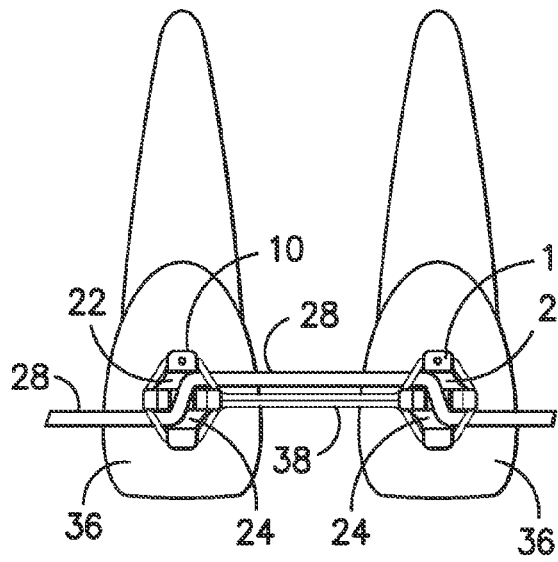
FIG. 9D shows a front view of two teeth, wherein each tooth includes a bracket in accordance with one aspect of the present invention, and wherein an archwire runs through the incisal slot on the outer portions of each bracket, up through the vertical slot, and through the gingival slot on each inner portion thereof, and wherein an elastic power chain is disposed about each bracket.
Figure 9E:
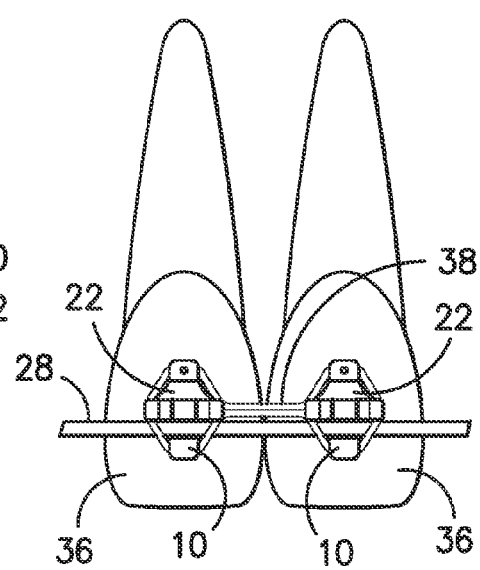
FIG. 9E shows a front view of the two teeth illustrated in FIG. 9D, showing the natural result and progression over time of the arrangement set forth in FIG. 9D.

The diamond-shaped tie-wing configuration on the brackets 10 allows multiple vectors of force to be applied to a tooth simultaneously. Prior orthodontic brace systems often apply force in only one direction or vector at a time. For instance, an orthodontist may employ a small to mid-sized archwire 28 with an elastic power chain 38 immediately upon installation of the braces on a patient in order to close a gap between adjacent teeth 36 by moving the crowns of the adjacent teeth together, as shown in FIGS. 9A and 9B. Then, in a later orthodontic appointment, the orthodontist may remove the mid-sized archwire 28 and replace it with sequential heavier gauge (stiffer) archwires 28 to move the roots of the teeth 36 into a more desirable position, as shown in FIG. 9C. The diamond-shaped tie-wing configuration, however, provides a means for imposing force vectors in multiple directions, as shown in FIG. 5. Thus, the two-step operation described above, in many cases, is unnecessary, and the correction and alignment of teeth using brackets with the diamond-shaped tie-wing configuration (as shown in FIGS. 9D and 9E) is much faster. In other words, the present configuration addresses teeth adjustments of the first order (in toward the tongue or out toward the cheek), second order (up or down, also known as gingival or incisal), the third order (torque), rotation, and angulation to be addressed simultaneously, which means the teeth can be straightened up and aligned more quickly, and potentially with fewer expensive and time-consuming visits to the orthodontist. Indeed, one major advantage to the present system is that patients are required to wear braces for a much shorter time period, because the simultaneous multi-vector approach reduces the steps and phases required by more conventional brace systems. Due to the fact that the present system is so versatile, it allows an orthodontist to maintain a much smaller inventory of brackets, which can result in significant cost savings for orthodontic practices.

Figure 7A:
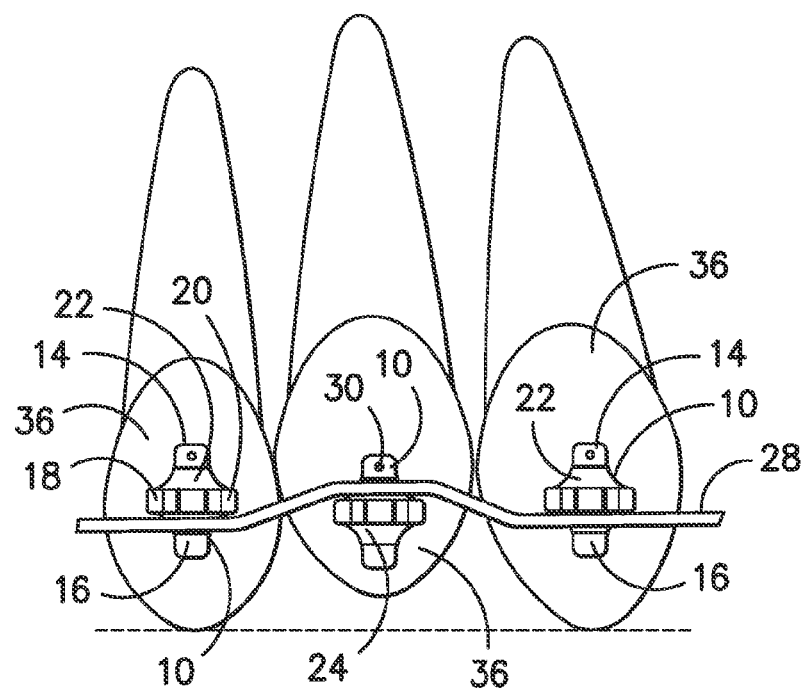
FIG. 7A is a front view of three teeth, each tooth bearing a bracket, and illustrating an archwire running through an incisal slot on the brackets of the two outer teeth, and runs through the gingival slot on the bracket of the middle tooth, in accordance with one aspect of the present invention.
Figure 7B:
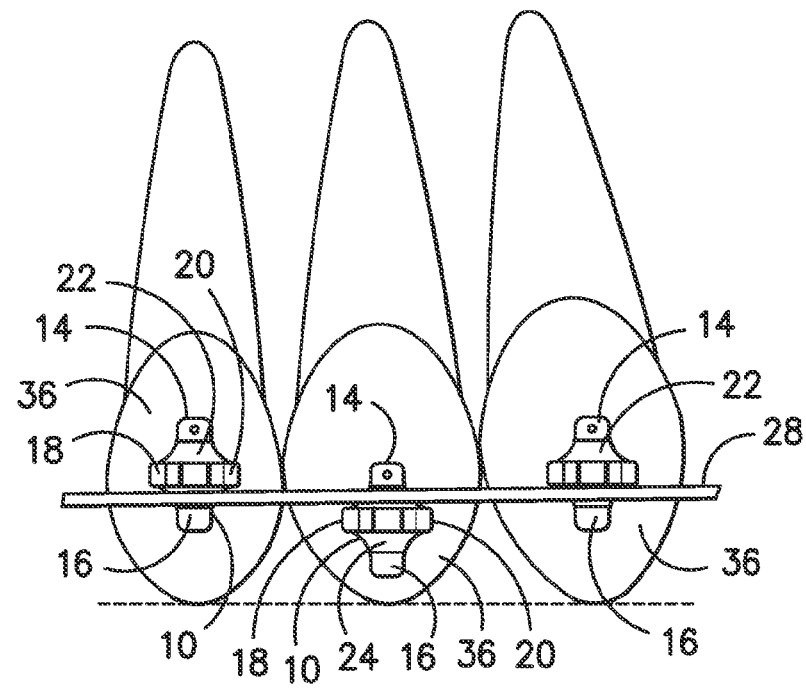
FIG. 7B is a front view of the three teeth set forth in 7A, wherein the middle tooth has been aligned into proper position in accordance with one aspect of the present invention.

Another advantage to the present system is that providing multiple archwire slots for each bracket drastically reduces the number of instances when an orthodontist must remove a bracket 10 from a tooth 36 and reattach it in a new position. There are many situations where, using the present system, the archwire 28 may simply be removed from one slot and replaced in the second slot without having to detach the bracket 10 from the tooth 36, thus saving time and expense. Also, if a diamond-shaped tie-wing bracket 10 is improperly placed on a tooth 36, an orthodontist may simply choose to use the most convenient slot, thus obviating the need to remove and reposition the bracket. For example, FIGS. 7A and 7B illustrate such a situation, where a bracket 10 on the center tooth 36 is slightly misplaced, because it was bonded to the tooth 36 before the tooth was fully erupted. In such a case, having the two parallel slots allows the orthodontist to use the more convenient gingival slot, rather than the incisal slot, thus saving time and effort for the orthodontist. Also, another advantage to the system is the need for fewer wires. Traditional braces may require as many as 9 archwires 28 during a progression whereas this new system would require merely 1 or 2 archwires 28.

Figure 8:
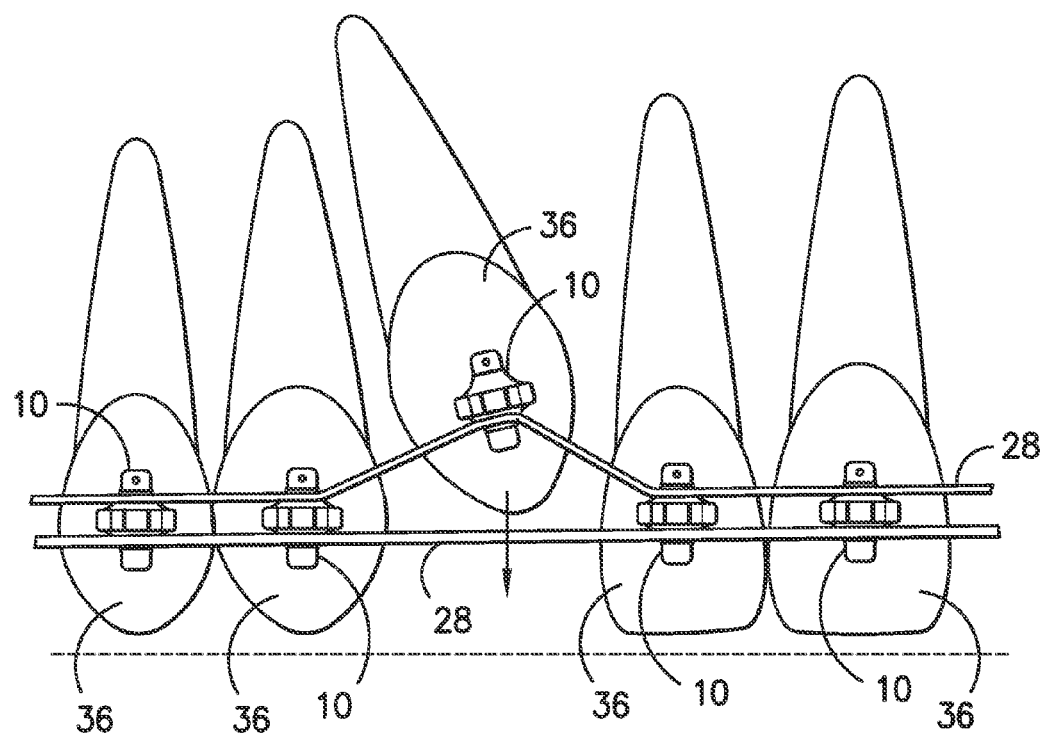
FIG. 8 is a front view of five teeth, each bearing a bracket, wherein the brackets on the outer four teeth include a heavy gauge base archwire through the incisal slot of each bracket, and wherein a secondary archwire is disposed in the gingival slots of the outer four teeth, and is disposed in the incisal slot of the middle tooth.

Further, in some cases, it is advantageous to use two archwires 28 simultaneously. For example, FIG. 8 shows a row of five teeth 36, wherein the middle tooth 36 is out of alignment, while the outer four teeth are properly aligned. Using brackets 10 having the diamond-shaped tie-wing configuration, a heavier gauge archwire 28 may be positioned within the incisal slots of the four outer teeth, in order to maintain proper alignment of those teeth. A secondary, smaller gauge archwire 28 may be positioned in the gingival slots of the outer four teeth, as shown, and through the incisal slot of the middle tooth bracket 10, in order to bring that tooth 36 into proper alignment without disrupting the alignment of the other four teeth.

Additionally, there are other circumstances and situations where it is advantageous to provide an orthodontic bracket system capable of utilizing two archwires simultaneously. For example, if one tooth is impacted (which means it is stuck in the bone, and has not penetrated the gum), an oral surgeon may uncover the crown of the impacted tooth, and then may bond a button with a gold chain to the impacted tooth. In that situation, a primary archwire may be applied to the brackets of the other teeth, excluding the impacted tooth, and a secondary archwire may be positioned through the second (typically incisal) slot of the other teeth, and may be connected to the impacted tooth to act as an eruption appliance (more commonly referred to as a traction loop). The traction loop is designed to pull the impacted tooth downwardly and outwardly. The advantage of this arrangement, of course, is that the primary archwire may maintain alignment of the other teeth, while the secondary archwire is used to properly guide and align the impacted tooth.

It should be understood that other features commonly associated with prior art orthodontic brace systems may be incorporated into the present invention, including ball hooks for elastics, which are typically available on the canine and premolar brackets. Power chains 38 may be used with the present invention as well, which work particularly well with the present invention, because the power chain 38 used with prior art brackets tends to rest on the archwire 28, causing friction and resistance to the desired force, while power chains 38 used in connection with the present invention do not come into contact (or are in minimal contact) with the archwire 28, thus eliminating the problem of undesirable friction therebetween, and by extension resulting in faster tooth movement.

Figure 11A:
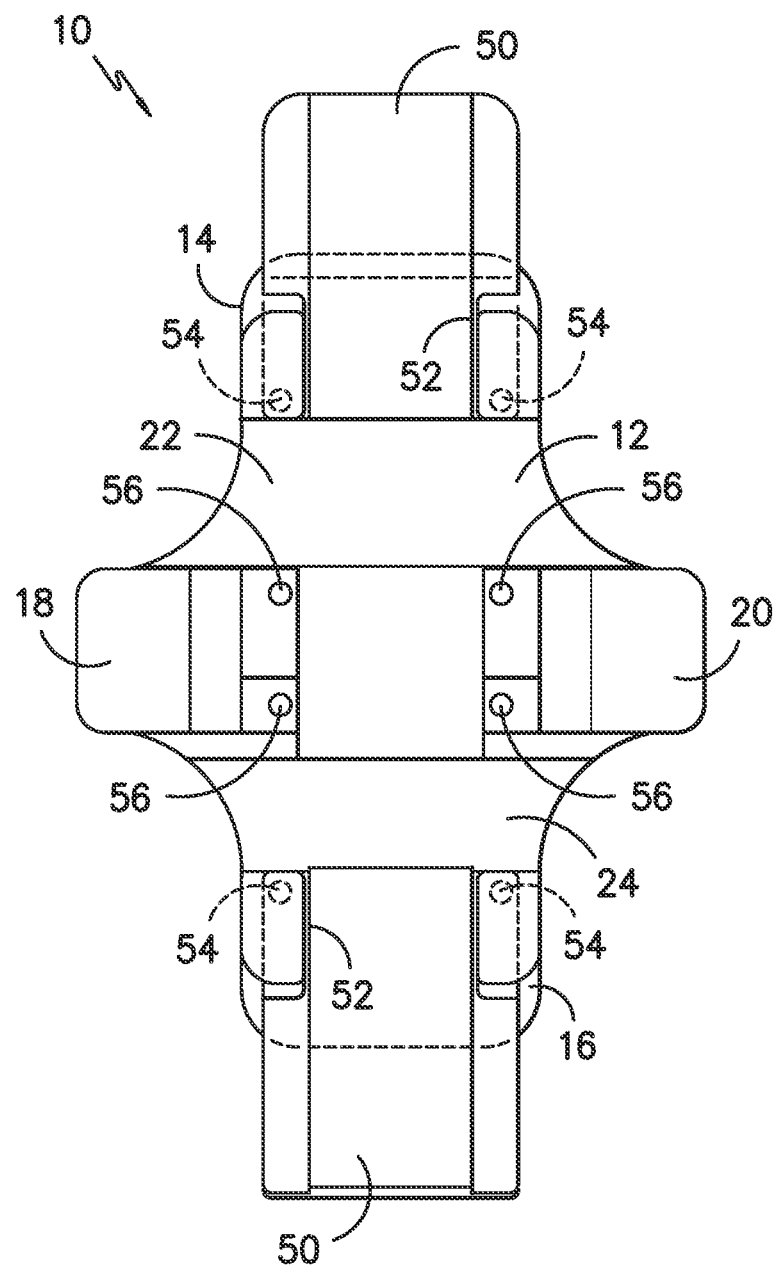
FIG. 11A shows a front view of an orthodontic bracket in accordance with another aspect of the present invention, including a pair of sliding doors, shown in an open position, which may slide and be secured into a closed position over the slots.

FIG. 11A shows another embodiment of an orthodontic bracket 10 having the diamond-shaped tie-wing configuration, further including a pair of sliding doors 50 that may be used to slide over the slots 24, 26 in order to secure an archwire (not shown) therein. In this embodiment, an upper door 50 is positioned within a channel 52 disposed on a front surface of the upper tie wing 14, and a lower door 50 is positioned within a channel 52 disposed on a front surface of the lower tie wing 16. Each door 50 includes a snap-fit mechanism including a pair of small round bulges 54, which are used to engage corresponding small divots 56 positioned on the left and right tie-wings 18, 20, so that each sliding door 50 may be snapped and secured into a closed position. Corresponding divots 56 are also positioned within the channel 52 of the upper and lower tie-wings 14, 16, so that the sliding doors 50 may be snap-fit into an open position, as well, for purposes of archwire insertion, adjustment, or replacement.

Figure 11D:
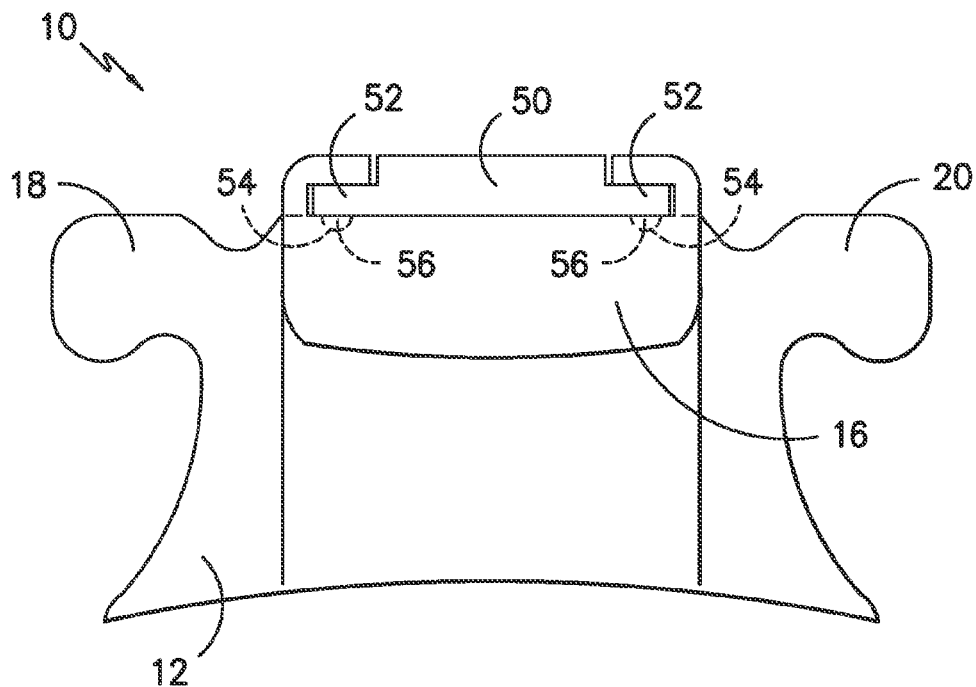
FIG. 11D shows a bottom view of an orthodontic bracket in accordance with the embodiment shown in FIGS. 11A-C.
Figure 11E:
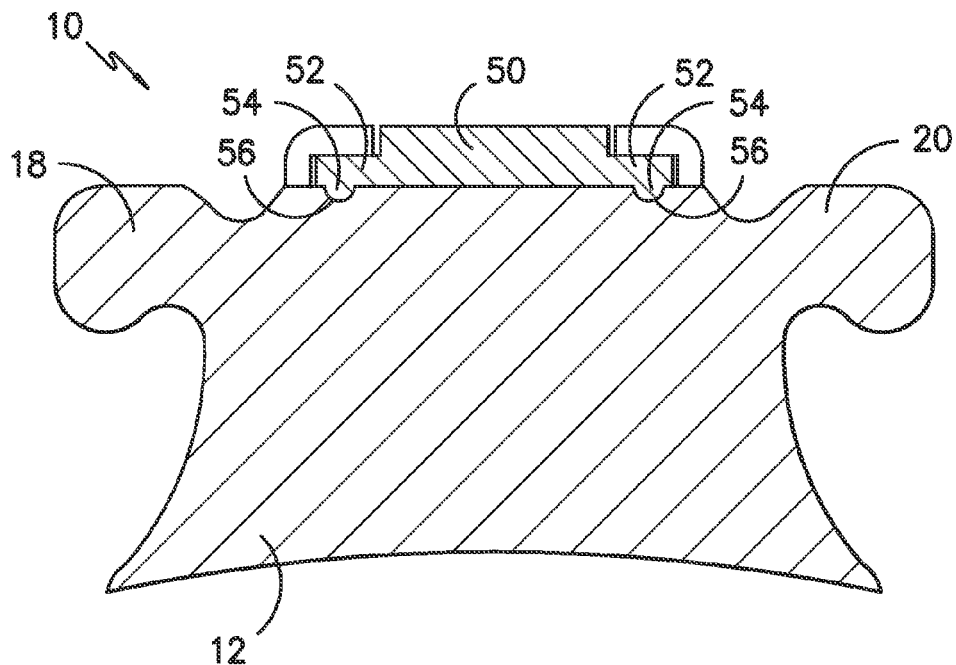
FIG. 11E shows a cross-sectional view of an orthodontic bracket in accordance with the embodiment shown in FIGS. 11A-D.

Such brackets 10 are called "self-ligating" brackets, because they do not require elastics or other means to secure the archwires within the slots 22, 24 of the bracket 10. The lower portions of the left and right tie-wings 18, 20 are slightly recessed, as shown in FIG. 11C, in order to accommodate the angle of the lower slot 24, so that the sliding door 50 may properly slide into a closed position and the snap-fit mechanism may be engaged. FIG. 11B shows the doors 50 in a closed position. FIG. 11D shows a bottom view of the self-ligating bracket 10, wherein the bottom sliding door 50 is positioned within the channel 52, and wherein the snap-fit mechanism is engaged in a closed position. Similarly, FIG. 11E shows a cross-sectional view of the sliding door 50 in a closed position over the slot 24 with the snap-fit mechanism engaged and secured.

FIGS. 12A and 12B show yet another embodiment of a self-ligating bracket 10, wherein a single sliding door 50 is disposed in a channel 52 that extends from a lower tie-wing 16, through an inner portion of the left and right tie-wings 18, 20, and ends within the upper tie-wing 14. The single sliding door 50 may be disposed in a closed position, as shown in FIG. 12A, or may be disposed in an open position, as shown in FIG. 12B, or any position therebetween. In a preferred embodiment, a snap-fit mechanism as described above may be used, wherein the door 50 includes a pair of small round bulges 54 that engage divots 56 positioned on the upper and lower tie-wings 14, 16, as shown. Alternatively, it is contemplated that the round bulges 54 may be positioned on the tie-wings, while the divots 56 may be positioned on the sliding door 50, on this or any other embodiment described herein.

Figure 13A:
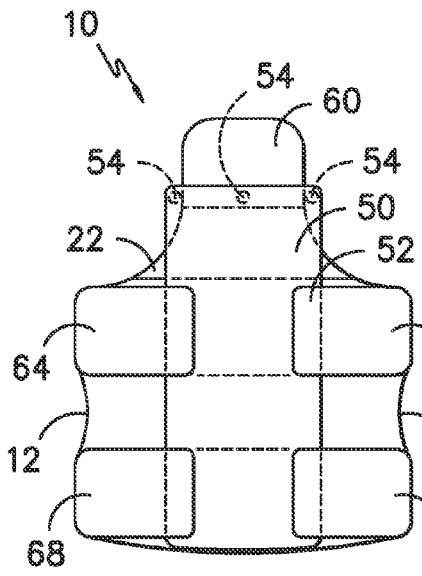
FIG. 13A shows a front view of an orthodontic bracket in accordance with another embodiment of the present invention, wherein the bracket includes five tie-wings and a pair of parallel horizontal slots, and further including a sliding door that is disposed in a closed position over both the upper and lower slots.

FIG. 13A illustrates another embodiment of a self-ligating bracket 10, wherein the bracket 10 includes five tie-wings: a top tie-wing 60, upper right and left tie-wings 62, 64, and lower right and left tie-wings 66, 68. Parallel horizontal slots 22, 24 are disposed between the tie-wings, wherein the upper slot 22 is disposed between the top tie-wing 60 and the upper left and right tie-wings 62, 64, and the lower slot 24 is disposed between the upper right and left tie wings 62, 64 on one side and the lower right and left tie-wings 66, 68 on the other. A sliding door 50 is positioned within a central channel 52 that extends between the lower tie wings 66, 68 and the upper tie wings 62, 64, and ending at the top tie-wing 60. Again, the snap-fit mechanism described above may be used to secure the sliding door 50 in an open position or a closed position.

Figure 13B:
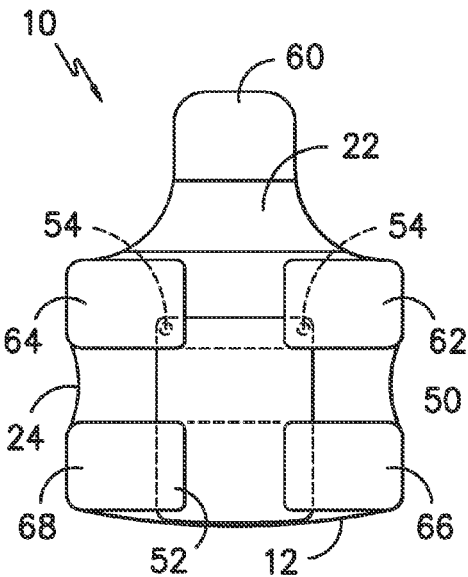
FIG. 13B shows a front view of an orthodontic bracket in accordance with another embodiment of the present invention, wherein the bracket includes five tie-wings and a pair of parallel horizontal slots, and further including a sliding door that is disposed in a closed position over the lower slot.

FIG. 13B is an alternate embodiment of a partially self-ligating bracket 10, wherein the tie-wing configuration is similar to that shown in FIG. 13A, but wherein the sliding door 50 is only used in conjunction with the lower slot 24, as shown. In this embodiment, the sliding door 50 is disposed within a channel 52, which only extends through the lower tie-wings 66, 68 and ends at the upper left and right tie-wings 62, 64. Additionally, if an archwire (not shown) is positioned within the upper slot 22 of the bracket 10 of this embodiment, elastics may be used to secure the archwire within the slot 22. The elastic may extend between either the top tie-wing 60 and the upper left tie-wing 64, or between the top tie-wing 60 and the upper right tie-wing 62, or may be disposed about all three tie-wings 60, 62, and 64, or may be disposed about all five tie-wings 60, 62, 64, 66, and 68.

Figure 13C:
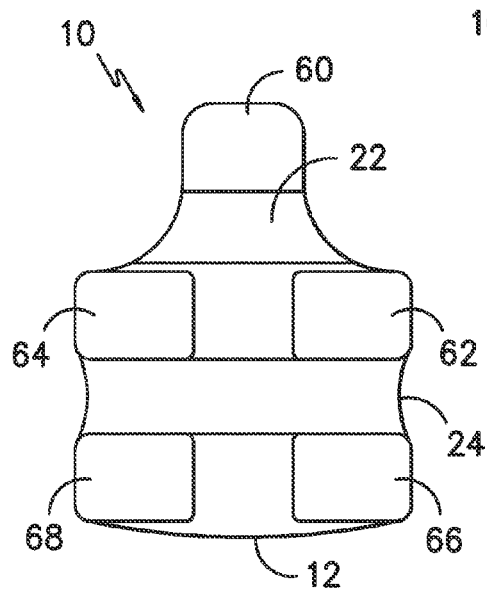
FIG. 13C shows a front view of an orthodontic bracket in accordance with another embodiment of the present invention, wherein the bracket includes five tie-wings and a pair of parallel horizontal slots.
Figure 13D:
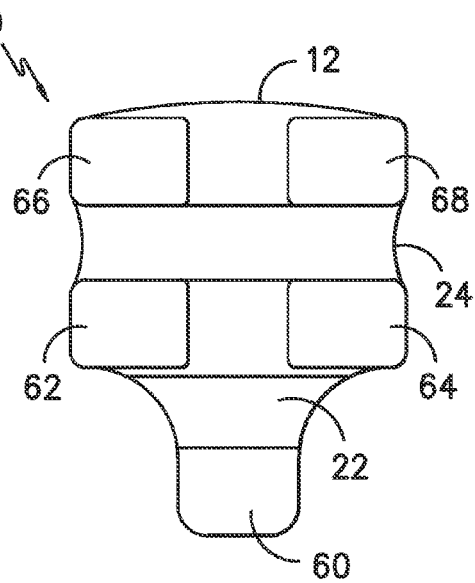
FIG. 13D shows a front view of an orthodontic bracket in accordance with another embodiment of the present invention, wherein the bracket includes five tie-wings and a pair of parallel horizontal slots.

FIGS. 13C and 13D show another alternate embodiment of an orthodontic bracket, wherein the tie-wings are configured similarly to those shown in FIGS. 13A and 13B, but which does not include the sliding door, and thus is not considered to be self-ligating. In this embodiment, elastics are used in the traditional manner, rather than the sliding doors, to secure the archwire within the slots of the bracket.

In order to use any of the self-ligating brackets shown and described herein, an orthodontist may attach the brackets 10 to a patient's teeth, slide the sliding doors 50 into an open position, and insert the archwire 28. Then, when the archwire 28 is in the proper position, the sliding doors 50 may be closed and secured in the closed position with the snap-fit mechanism, or by using any other means for securing the sliding doors 50 into the closed position. For adjustment or replacement of the archwire, the orthodontist may open the sliding door 50 to any particular bracket (or multiple brackets), adjust, remove or replace the archwire disposed therein, and then return the sliding door 50 to the closed position. It is also contemplated that the doors may be hinged, rather than sliding.

One of the main purposes of the self-ligating brackets is to avoid the use of elastic modules, thereby eliminating the friction from the elastic modules which would result in faster tooth movement. Additionally, the sliding doors 50 of the self-ligating brackets provide a smoother and sleeker orthodontic look for the patient, and provide a less-plaque-retentive surface than elastics provide resulting in a more hygienic orthodontic appliance.

Although the present invention has been described in considerable detail with reference to certain preferred versions thereof, other versions are possible. Therefore, the spirit and scope of the appended claims should not be limited to the description of the preferred versions contained herein. All features disclosed in this specification may be replaced by alternative features serving the same, equivalent or similar purpose, unless expressly stated otherwise. Thus, unless expressly stated otherwise, each feature disclosed is one example only of a generic series of equivalent or similar features.

What is claimed is:
1. An orthodontic brace system comprising:
 a plurality of brackets, wherein each said bracket is adapted to be adhered to a patient's tooth, and wherein at least one of said brackets includes a base member and four tie-wings in a diamond-shaped configuration, including a single upper tie-wing, a single lower tie-wing, and a left and right tie-wing disposed therebetween, and wherein said diamond-shaped tie-wing configuration defines a pair of parallel, horizontal slots including an upper slot and a lower slot;
 said bracket further defining a channel extending at least partially through said tie-wings;
 a first sliding door positioned within said channel, so that said sliding door may slide between a closed configuration over at least one of said slots and an open position that provides access to said at least one of said slots; and
 an archwire that is adapted to be received and secured within said diamond-shaped bracket, either through said upper slot, said lower slot, or a combination thereof.

2. The orthodontic brace system set forth in claim 1, further comprising a plurality said brackets having said diamond-shaped tie-wing configuration.

3. The orthodontic brace system set forth in claim 1, wherein said sliding door extends in a closed position over both said upper slot and said lower slot.

4. The orthodontic brace system set forth in claim 1, further including a second sliding door disposed within said channel; wherein said first sliding door extends over said lower slot in a closed position and said second sliding door extends over said upper slot in a closed position, and so that each said sliding door may slide into an open position in order to provide access to said slots.

5. The orthodontic brace system set forth in claim 4, wherein said channel includes a first angle and a second angle, wherein said first door is disposed within said channel at said first angle, and said second door is disposed within said channel at said second angle.

6. The orthodontic brace system set forth in claim 1, wherein said sliding door and said tie-wings include a snap-fit mechanism to hold said sliding door in either an open or closed position.

7. The orthodontic brace system set forth in claim 6, wherein said snap-fit mechanism includes at least one generally circular bulge that corresponds with and engages a divot.

8. The orthodontic brace system set forth in claim 7, wherein said generally circular bulge is positioned on said sliding door, and said divot is positioned on one of said tie-wings.

9. The orthodontic brace system set forth in claim 7, wherein said generally circular bulge is positioned on one of said tie-wings and said divot is positioned on said sliding door.

10. An orthodontic bracket comprising:

a base member;

five tie-wings extending from said base member, said tie-wings defining a pair of parallel, horizontal slots, including an upper slot and a lower slot, each said slot being adapted to receive an archwire;

said bracket defining a channel between at least two of said tie-wings;

a sliding door disposed within said channel, so that said sliding door extends over at least one of said slots when said sliding door is in a closed position.

11. The orthodontic brace set forth in claim 10, wherein said sliding door extends over both of said slots when said sliding door is in a closed position.

12. The orthodontic brace system set forth in claim 11, wherein said sliding door and said tie-wings include a snap-fit mechanism to hold said sliding door in either an open or closed position.

13. The orthodontic brace system set forth in claim 12, wherein said snap-fit mechanism includes at least one generally circular bulge that corresponds with and engages a divot.

14. The orthodontic brace system set forth in claim 13, wherein said generally circular bulge is positioned on said sliding door, and said divot is positioned on one of said tie-wings.

15. The orthodontic brace system set forth in claim 13, wherein said generally circular bulge is positioned on one of said tie-wings and said divot is positioned on said sliding door.

* * * * *